United States Patent [19]

Kamo et al.

[11] Patent Number: 4,641,096
[45] Date of Patent: Feb. 3, 1987

[54] NUCLEAR MAGNETIC RESONANCE SPECTROMETRY

[75] Inventors: Osamu Kamo; Muneki Ohuchi; Kazuhiro Matsushita, all of Tokyo, Japan

[73] Assignee: JEOL Ltd., Tokyo, Japan

[21] Appl. No.: 674,733

[22] Filed: Nov. 26, 1984

[30] Foreign Application Priority Data

Nov. 30, 1983 [JP] Japan .................. 58-226340

[51] Int. Cl.$^4$ .......................................... G01R 33/20
[52] U.S. Cl. ..................................... 324/311; 324/307
[58] Field of Search ......... 324/300, 307, 308, 309–314

[56] References Cited

U.S. PATENT DOCUMENTS

| 4,045,723 | 8/1977 | Ernst | 324/309 |
|---|---|---|---|
| 4,345,207 | 8/1982 | Bertrand | 324/314 |
| 4,443,761 | 4/1984 | Levitt | 324/311 |
| 4,470,014 | 9/1984 | Levitt | 324/307 |
| 4,477,777 | 10/1984 | Gordon | 324/300 |
| 4,502,008 | 2/1985 | Ohuchi | 324/307 |
| 4,510,449 | 4/1985 | Ernst | 324/309 |
| 4,521,732 | 6/1985 | Pegg | 324/308 |

OTHER PUBLICATIONS

"Pulse Sequence for the Generation of a $^{13}$C Subspectrum of Both Aromatic and Aliphatic Quaternary Carbons" by M. Robin Bendall et al., Journal of Chemical Society, Chemical Communications, 1982, pp. 1138–1140.

Primary Examiner—Michael J. Tokar
Attorney, Agent, or Firm—Webb, Burden, Robinson & Webb

[57] ABSTRACT

A nuclear magnetic resonance spectrometry is disclosed in which a 90° pulse and a 180° pulse are applied to nuclei under observation at a time interval of t. Then, the resulting echo signal is observed after a period of t. Either a strong 90° pulse of strong RF waves are applied to nuclei that are not observed. The strong RF waves decouple the nuclei not observed over a broad range. The application of the strong 90° pulse or RF waves is initiated in synchronism with the 180° pulse. The application of the RF waves are terminated before the beginning of the observation of the echo signal. The observation made in this way makes it possible to obtain spectra of quaternary carbons, the spectra including the information about long-range coupling.

5 Claims, 17 Drawing Figures

Fig. 1(a)    Fig. 1(b)    Fig. 1(c)
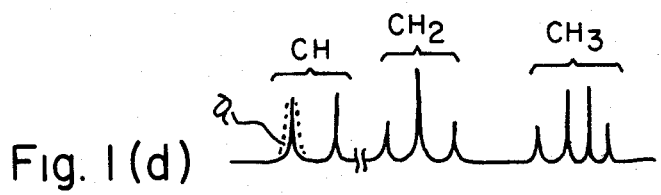
Fig. 1(d)
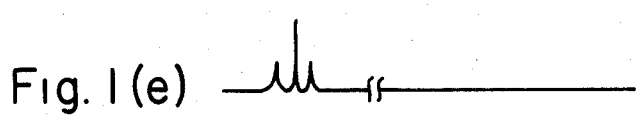
Fig. 1(e)
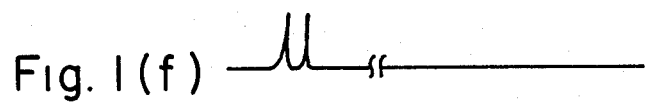
Fig. 1(f)
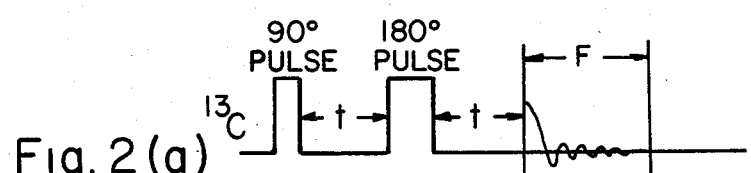
Fig. 2(a) $^{13}C$
Fig. 2(b) $^{1}H$
PRIOR ART

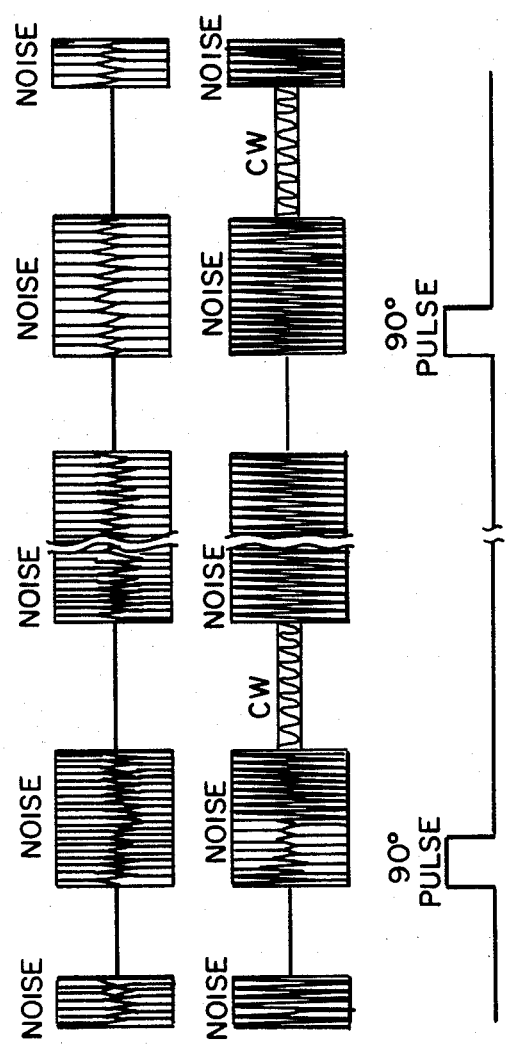

NUCLEAR MAGNETIC RESONANCE SPECTROMETRY

BACKGROUND OF THE INVENTION

The present invention relates to a nuclear magnetic resonance spectrometry method and, more particularly, to a nuclear magnetic resonance spectrometry method for observing quaternary carbons.

When the structure of an organic compound is analyzed by obtaining a $^{13}C$ NMR spectrum from it, the determination of the number of hydrogen atoms coupled to each carbon and the subsequent analysis of the chemical shifts of the carbons which are caused by the hydrogens must always be performed. In $^{13}C$ NMR spectra where carbons remain coupled to hydrogen nuclei, a line due to methyl group ($CH_3$) splits into a quartet (FIG. 1(a)), a line due to methylene group ($CH_2$) splits into a triplet (FIG. 1(b)), and a line due to methine group (CH) splits into a doublet (FIG. 1(c)). Quaternary carbons (cation linked to four other C atoms) which are not coupled to any hydrogen nucleus appear as a singlet. Thus, it is possible to determine from this manner of splitting how many hydrogens are coupled to each carbon. However, in case where a singlet $\alpha$ of quaternary carbons is superimposed on a quartet, a triplet, or a doublet which is attributable to $CH_3$, $CH_2$, or CH, as shown in FIG. 1(d), it is likely that the peaks of the quaternary carbons are overlooked.

A method has been proposed which extracts and observes only the subspectra of quaternary carbons. Referring to FIG. 2a and FIG. 2b, the timings at which RF pulses are applied to carbon nuclei as well as the timing at which the resulting signal is observed are shown in FIG. 2a. The timing at which a decoupling RF pulse is applied to hydrogen nuclei is shown in FIG. 2b. The resulting free induction decay signal, or an echo signal, is sampled for a period of F. The signal is noise-modulated for the period indicated by the hatching. This pulse sequence removes all the peaks of CH, $CH_2$, $CH_3$, etc. other than the peaks of quaternary carbons from the spectrum. This technique is described, for example, in J. Chem. Soc., Chem. Commun., 1982, pp. 1138–1140.

According to this prior art pulse sequence, hydrogen nuclei are fully decoupled. Therefore, fine splitting of the peaks of quaternary carbons which would otherwise be caused by the long-range, weak coupling between the quaternary carbons and the adjacent hydrogen nuclei cannot be observed. As a result, it is utterly impossible to know how many hydrogen atoms exist near the quaternary carbons.

SUMMARY OF THE INVENTION

In view of the foregoing difficulty, it is the object of the present invention to provide a nuclear magnetic resonance spectrometry method which is capable of yielding spectra of quaternary carbons, the spectra including the information about the aforementioned long-range coupling.

The spectrometry method according to the invention comprises the steps of applying a 90° pulse and a 180° pulse at the resonant frequency of the nuclei under observation. The pulses are spaced at a time interval of t. Then the resulting echo signal is observed after another time interval of t. In one embodiment, this method is characterized in the application of a strong 90° pulse at the resonant frequency of the nuclei that are not to be observed. This pulse is started in synchronism with the 180° pulse applied to the nuclei under observation. In another embodiment, strong radiofrequency waves for decoupling the nuclei not to be observed are applied over a wide range starting in synchronism with the 180° pulse applied to the nuclei under observation and terminated before the observation of the echo signal. In a preferred embodiment of either the first or second embodiments above set forth, weak RF waves of the resonant frequency not to be observed are applied during the observation period.

BRIEF DESCRIPTION OF THE DRAWINGS

FIGS. 1(a)–1(d) are diagrams showing the splitting of peaks derived from methyl, methylene, and methine;

FIGS. 1(e) and (f) are expanded peak $\alpha$ in FIG. (d);

FIG. 2 is a diagram showing a pulse sequence previously proposed;

FIGS. 5, 6, and 7 are timing diagrams for alternative embodiments.

DESCRIPTION OF THE PREFERRED EMBODIMENT

Figure 3:
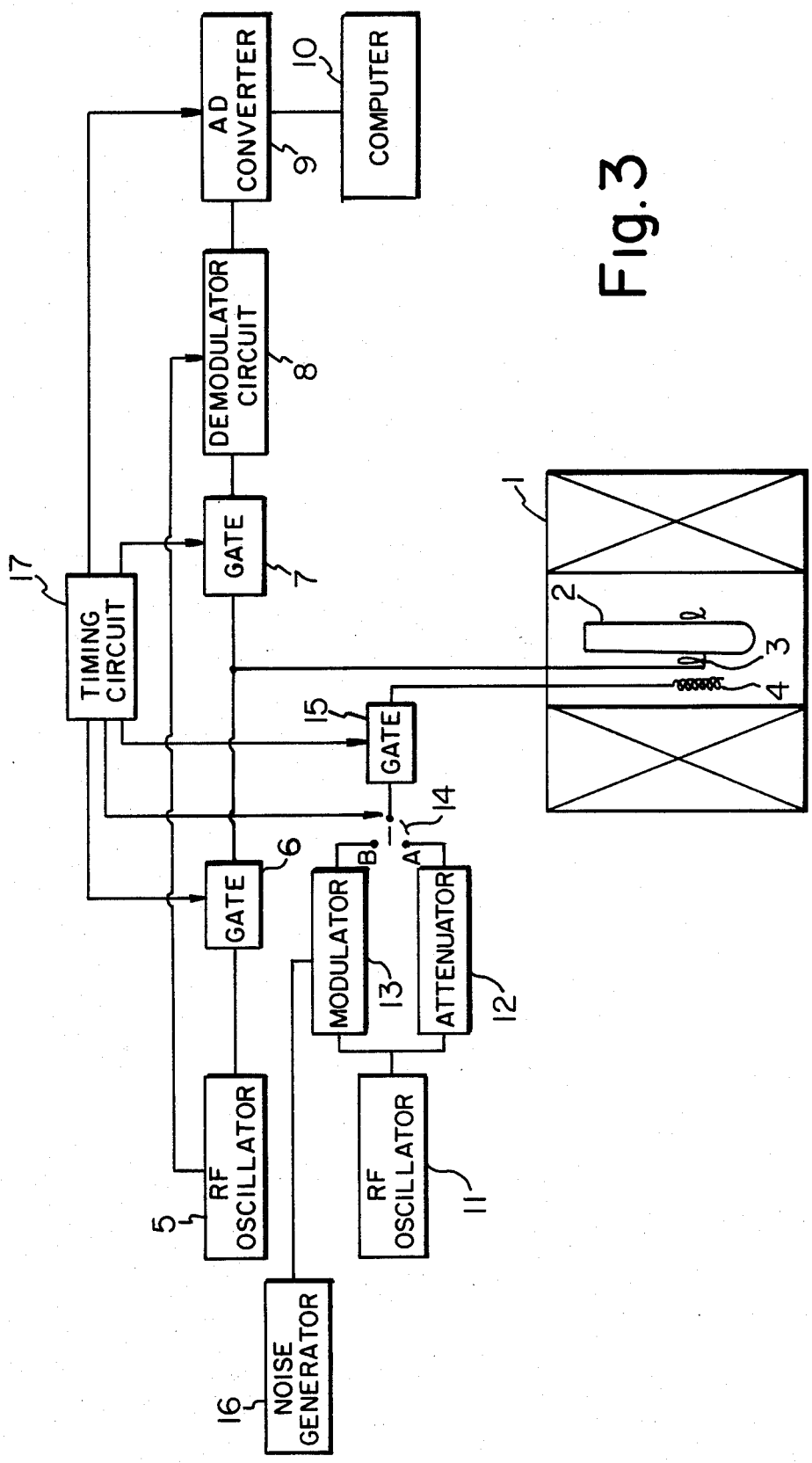
FIG. 3 is a block diagram of a nuclear magnetic resonance spectrometer used to execute the method according to the present invention.

Referring to FIG. 3, there is shown a nuclear magnetic resonance spectrometer embodying the concept of the present invention. This spectrometer includes a magnet 1 that produces a static magnetic field, in which a sample tube 2 is placed. The spectrometer further includes a transmitter/receiver coil 3 surrounding a sample, a decoupling transmitter coil 4, an RF oscillator 5, gates 6 and 7, a demodulator circuit 8, an analog-to-digital converter 9, and a computer 10. The RF waves which are generated by the oscillator 5 for observation of the sample are supplied as an RF pulse to the transmitter/receiver coil 3 via the gate 6. The application of the RF pulse to the sample is accompanied by a resonance, which, in turn, induces a resonance signal in the coil 3. The resonance signal is fed via the gate 7 to the demodulator circuit 8, where it is demodulated. The resulting free induction decay signal is furnished via the A/D converter 9 to the computer 10, in which it is stored and processed by Fourier transformation.

A decoupling RF oscillator 11 produces decoupling radio-frequency waves, which are fed to the decoupling transmitter coil 4 via an attenuator 12 or a modulator 13, a switching circuit 14, and a gate 15. A noise generator 16 produces a noise signal to the modulator 13. The gates 6, 7, and 15 are enabled or disabled under the control of a timing circuit 17. The sampling operation of the A/D converter 9 and the switching operation of the switching circuit 14 are also performed under the control of the timing circuit 17.

Figure 4:
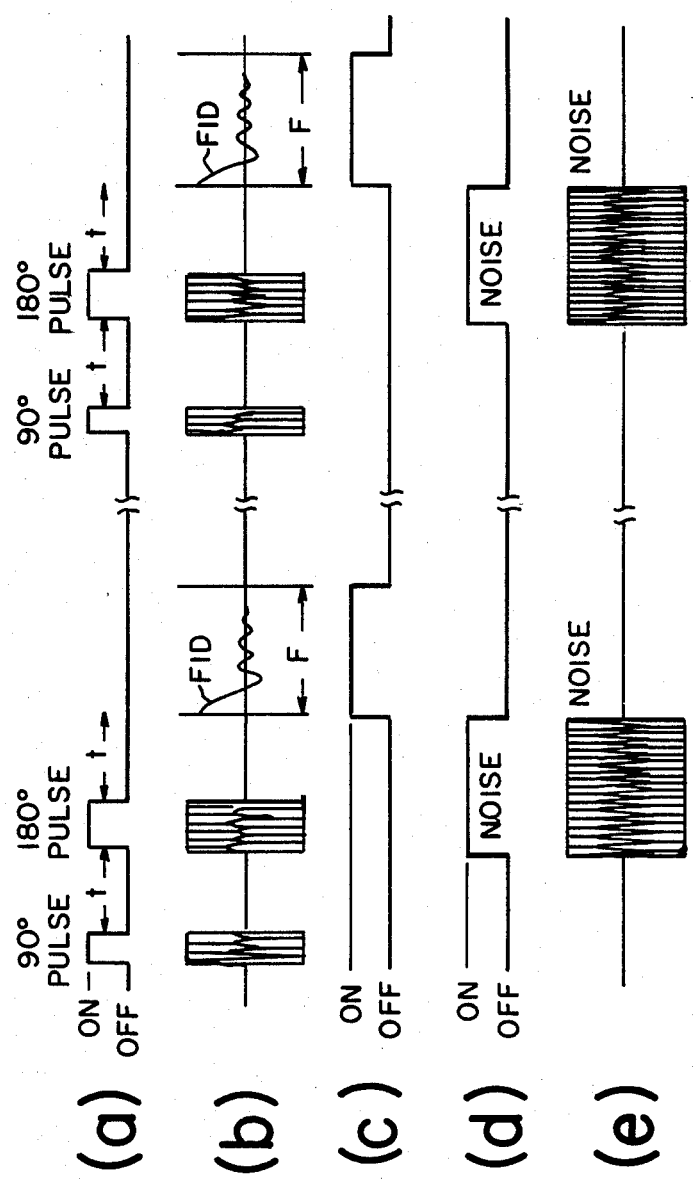
FIGS. 4(a) to 4(e) are timing diagrams for illustrating the operation of the spectrometer shown in FIG. 3.

The operation of the apparatus constructed as described above is next described by referring to FIGS. 4(a) to 4(e). The timing signal from the timing circuit 17 enables or disables the gate 6 at the timing shown in FIG. 4(a), permitting 90° pulses and 180° pulses to be applied to the sample at intervals of t for observing $^{13}C$, as shown in FIG. 4(b). The free induction decay signal which is produced after a period of t has elapsed since the application of each 180° pulse is passed through the gate 7 that is enabled at the timing shown in FIG. 4(c).

The signal is then sampled at the same timing by the A/D converter 9, and is stored in the computer 10.

Meanwhile, on the side of the oscillator 11, the switching circuit 14 is switched to contact B, and the gate 15 is enabled concurrently with the 180° pulse and disabled immediately before each observation begins, as shown in FIG. 4(d). Thus, as shown in FIG. 4(e), sufficiently strong decoupling RF waves whose frequency range has been extended by noise modulation are applied to the sample for the period during which the gate 15 is enabled. During the observation periods F, the RF waves are not applied.

Thus, according to the novel method, intense coupling RF waves are not applied to the sample during each observation period. Consequently, all the peaks attributed to methine, methylene, methyl, etc. are suppressed, but the peaks of quaternary carbons are left, as shown in FIG. 1(e). Further, since decoupling is not done during each observation period, the peaks of the quaternary carbons exhibit fine splitting over a range of the order of several Hertz due to the long-range coupling with the surrounding hydrogen atoms. The obtained spectrum offers information about the hydrogen atoms that are adjacent to the quaternary carbons.

Referring to FIG. 5, there is shown another example in which strong decoupling RF waves that are noise-modulated are applied to the sample during the period beginning with the end of one observation and ending with the beginning of the next observation, in addition to the waves shown in FIG. 4(e). The application of the strong RF waves having a broad range of frequencies for non-observation periods causes nuclear Overhauser effects, intensifying the induction decay signals. Hence, the spectra that are obtained after Fourier transformation are large in intensity over the whole range, thus facilitating the analysis.

Additional RF waves are employed in the example of FIG. 6. In particular, the additional RF waves have a quite small magnitude and act to selectively decouple the carbons from hydrogen nuclei during observation periods F. For this purpose, the selecting circuit 14 is switched to contact A during each observation period, and the RF waves are applied to the sample via the gate 15 after reducing the level of the waves, for example, by two or three orders of magnitude. The frequencies of the decoupling RF waves are so selected that they correspond to some peaks of a previously obtained $^1$H NMR spectrum, the peaks being supposed to indicate the vicinities of quaternary carbons. Thus, the application of the quite weak RF waves during each observation period breaks the coupling with only the selected hydrogen atoms. In this way, the spectrum of FIG. 1(e) is changed to the spectrum of FIG. 1(f), thus enabling one to analyze the hydrogen atoms lying close to quaternary carbons.

In the above example, the noise-modulated decoupling RF waves are continuously applied to the sample, as shown in FIGS. 4(e), 5 or 6. Alternatively, 90° pulses for hydrogen nuclei may be applied in synchronism with the 180° pulses for carbon nuclei, as shown in FIG. 7, corresponding to the example of FIG. 2. This alternative method will yield similar advantages.

Having thus described the invention with the detail and particularity required by the Patent Laws, what is desired protected by Letters Patent is set forth in the following claims.

We claim:

1. A nuclear magnetic spectrometry method comprising the steps of:

applying a 90° RF pulse and a 180° RF pulse, said pulses of frequency to affect the nuclei under observation, said 90° and 180° pulses separated by a time interval of t, observing the resulting echo (FID) signal after another time interval of t, and applying a decoupling signal comprising a strong noise-modulated RF signal of a frequency to affect nuclei that are not to be observed, the strong noise-modulated RF signal acting to decouple the nuclei not observed over a broad range, the application of the RF decoupling signal being terminated before the beginning of the observation of the echo signal.

2. A nuclear magnetic resonance spectrometry method as set forth in claim 1, wherein the observation is carried out repeatedly, and wherein the strong RF waves are continuously applied to decouple nuclei not to be observed over a broad range during each period that begins with the end of the observation of one echo signal and ends with the next application of the 90° pulse of a frequency to affect the nuclei under observation.

3. A nuclear magnetic resonance spectrometry method as set forth in claim 1, wherein weak RF waves having the same frequencies as the resonance frequencies of the nuclei not observed are applied at least for the period during which the echo signal is observed.

4. A nuclear magnetic spectrometry method comprising the steps of:

applying a 90° RF pulse and a 180° RF pulse, said pulses of frequency to affect the nuclei under observation, said 90° and 180° pulses separated by a time interval of t, observing the resulting echo (FID) signal after another time interval of t, and applying a decoupling signal comprising a strong 90° RF pulse of a frequency to affect nuclei that are not to be observed in synchronism with the 180° pulse applied to the nuclei under observation.

5. A nuclear magnetic resonance spectrometry method according to claim 1 wherein the strong noise-modulated pulse is applied at least during the 180° pulse applied to the nuclei under observation.

* * * * *